US00PP34240P2

(12) United States Plant Patent
Bradford et al.

(10) Patent No.: US PP34,240 P2
(45) Date of Patent: May 17, 2022

(54) PEACH TREE NAMED 'RED PRINCESS IV'

(50) Latin Name: *Prunus persica*
Varietal Denomination: RED PRINCESS IV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,916

(22) Filed: Dec. 17, 2021

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./194, 197
See application file for complete search history.

(56) References Cited

U.S. PATENT DOCUMENTS

PP28,338 P3 8/2017 Bradford

*Primary Examiner* — Susan McCormick Ewoldt

(57) ABSTRACT

The present invention relates to a new and distinct variety of peach tree, *Prunus persica*, broadly characterized by a medium size, vigorous, hardy, self-fertile, productive and regular bearing tree. The variety blooms during the very early blooming season and requires about 250 chilling hours. The fruit matures under the ecological conditions described in late May with the first picking on May 27, 2021. The fruit is uniform, large in size, oblate in shape, clingstone in type, non-melting and firm in texture, yellow with red bleeding in flesh color, dark red skin color, and traditional peach in flavor.

1 Drawing Sheet

Botanical classification: *Prunus persica.*
Variety denomination: 'RED PRINCESS IV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'RED PRINCESS IV'.

During the fruit season of 2011 we gathered fruit from many of our newest and best selections to grow their open pollinated seeds. One group of the early maturing peaches was gathered, and the seeds were removed, cracked, stratified, germinated as a group with the label "Ey YP (OP)", and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2016 we selected the present variety as a single tree from the group of seedlings described above. Subsequent to origination of the present variety of peach tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is most similar to 'Red Princess II' peach (U.S. Plant Pat. No. 28,338) by blooming in the early season, by having large blossoms, by being self-fertile, by having reniform leaf glands, and by producing peaches that are clingstone in type, mostly red in skin color, oblate in shape, traditional peach in flavor, and non-melting in texture, but is distinguished therefrom by having a larger and more vigorous tree, by requiring less chilling hours, and by producing fruit that has more red bleeding in the flesh color, that is larger in size, that has a sweet instead of bitter kernel, and that matures about five days later.

SUMMARY OF VARIETY

In summary, the present peach variety is characterized by a medium size, vigorous, hardy, self-fertile, productive and regular bearing tree. The variety blooms during the very early blooming season and requires about 250 chilling hours. The fruit matures under the ecological conditions described in late May with the first picking on May 27, 2021. The fruit is uniform, large in size, oblate in shape, clingstone in type, non-melting and firm in texture, yellow with red bleeding in flesh color, dark red skin color, and traditional peach in flavor.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower buds and blossoms as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 4, 2021, on the original tree during its tenth growing season. The blossom and flower descriptions were made the previous blooming season. All major color code designations are by reference to the Inter-Society Color Council, National Bureau of Standards. Common color names are also used occasionally.

PARENTAGE

Seed parent: Unknown.
Pollen parent: Unknown.

TREE

Size: Medium, reaching and maintaining a height of 10' [3.05 m.] and a spread of 9' [2.74 m.] after ten growing seasons utilizing typical dormant pruning.
Vigor: Vigorous, responding typically to irrigation and fertilization. The variety grows about 2' [0.61 m.] of surplus top-growth during the spring and summer. The plant should be grown on a standard commercial rootstock for production purposes.
Growth: Spreading and moderately dense.
Form: Pruned to vase form.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Approximate chilling requirement: 250 hours.
Leaf bud burst: Early, just after the start of flowering.
Trunk:
- *Size*.—Medium, reaching a maximum diameter of 5¾" [146 mm.] after the tenth growing season.
- *Texture*.—Medium, shaggy.
- *Bark color*.—A Grayish yellowish brown [80. gy.yBr] and Moderate yellowish brown [77. m.yBr] variegation with Dark grayish yellowish brown [81. d.gy.yBr] crevices present.
- *Lenticels*.—Approximate Number Per Square Inch: 10. Color: Light brown [57. l.Br]. Average Size: ¼" [6.4 mm.] in length. The width is typically one fourth as much as the length. Shape: Elongated.

Branches:
- *Size*.—Medium, diameter of main scaffold is 2¾" [69.9 mm.] measured 12" above the crotch, diameter of limb is 1¾" [44.5 mm.] measured 12" above the first fork.
- *Texture*.—Smooth to medium on first and second year wood, increasing roughness with age.
- *Color*.—1st Year Wood Topside: Grayish red [19. gy.R]. 1st Year Wood Underside: Brilliant yellow green [116. brill.YG]. Older Wood: A Light grayish yellowish brown [79. l.gy.yBr] and Grayish yellowish brown [80. gy.yBr] variegation with Dark yellowish brown [78. d.yBr] crevices present.
- *Lenticels*.—Number Per Square Inch: About 20 on second year wood. Color: Light grayish yellowish brown [79. l.gy.yBr]. Average Size: Small, 1/16" [1.6 mm.] in length. The width is typically one fourth as much as the length. Shape: Elongated.

Leaves:
- *Size*.—Medium. Average Length: 5¼" [133.4 mm.]. Average Width: 1½" [38.1 mm.].
- *Arrangement*.—Alternate.
- *Thickness*.—Medium.
- *Form*.—Elliptical.
- *Apex*.—Acuminate.
- *Base*.—Rounded to acute with and average base angle of 75 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Light greenish yellow [101. l.gY].
- *Petiole*.—Average Length: ½" [12.7 mm.]. Average Thickness: 1/16" [1.6 mm.]. Color: Strong yellow green [117. s.YG].
- *Stipules*.—Number: Usually 2 per leaf, up to 6 per growing tip. Average Length: ¼" [6.4 mm.]. Color: Vivid yellow green [115. v.YG] becoming Dark olive brown [96. d.OlBr] with age.
- *Glands*.—Number: 2 to 4 per leaf. Position: Alternate positioned near the intersection of petiole and base of blade. Form: Reniform. Size: Medium, about 1/48" [0.5 mm.] in length. Color: Moderate olive green [125. m.OlG] acquiring a Dark olive brown [96. d.OlBr] center with age.
- *Leaf buds*.—Pointed.

Flower buds:
- *Hardiness*.—Hardy, with respect to central California blooming season.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Pale purplish pink [252. p.pPk].

Flowers: Perfect, complete, perigynous, usually a single pistil, about thirty stamens, five sepal and petal locations alternately positioned.
- *Type*.—Showy, large.
- *Average flower diameter*.—1⅝" [41.3 mm.].
- *Average flower depth*.—½" [12.7 mm.] when fully open.
- *Number of petals*.—Five, extra petal fragments rarely observed, double blossoms not observed.
- *Petal arrangement*.—Overlapping.
- *Petal shape*.—Circular to oval.
- *Petal margin*.—Entire, wavy.
- *Average petal diameter*.—⅝" [15.9 mm.].
- *Average petal length*.—11/16" [17.5 mm.].
- *Petal apex*.—Rounded.
- *Petal base*.—Rounded.
- *Petal color*.—Light pink [4. l.Pk] toward the apex and Moderate pink [5. m.Pk] toward the base on both sides on most flowers, but a few flowers have Brilliant purplish pink [246. brill.pPk] petals.
- *Anthocyanin coloration intensity*.—Weak.

*Anther color*.—Moderate reddish orange [37. m.rO] surrounding a Light yellow [86. l.Y] center at bloom onset.
*Pollen*.—Anthers produce an abundance of Brilliant yellow [83. brill.Y] pollen.
*Stigma color*.—Light greenish yellow [101. l.gY].
*Stigma position*.—Typically located slightly above the nearby anthers.
*Stamen position*.—Typically located about 1/16" [1.6 mm] below the petals.
*Average pistil length*.—3/4" [19.1 mm.].
*Average stamen length*.—9/16" [14.3 mm.].
*Ovary*.—Pubescent.
*Sepal color*.—Deep purplish red [256. deep pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—3/8" [9.5 mm.].
*Sepal width*.—1/4" [6.4 mm.].
*Sepal apex*.—Rounded to elliptical to match the sepal length and width.
*Sepal margin*.—Fairly smooth.
*Sepal outer surface*.—Pubescent.
*Fragrance*.—Moderate.
*Blooming period*.—Very early, blooms at the same time as 'Spring Princess' (U.S. Plant Pat. No. 17,750) peach.
*Onset of bloom*.—One percent on Feb. 3, 2021.
*Date of full bloom*.—Feb. 15, 2021.
*Duration of bloom*.—One to two weeks, dependent on ambient temperature.
*Bloom density*.—Medium to heavy.
*Number per cluster*.—1 to 3 with single flowers most common.

FRUIT

Maturity when described: Firm ripe, Jun. 4, 2021.
Date of first picking: May 27, 2021.
Date of last picking: Jun. 12, 2021.
Size: Uniform, large.
*Average diameter axially*.—2 3/4" [69.9 mm.].
*Average diameter across suture plane*.—3 3/8" [85.7 mm.].
*Average diameter across cheek plane*.—3 3/8" [85.7 mm.].
*Typical weight*.—9.9 ounces [282 grams].
Form: Mostly uniform, oblate.
*Longitudinal section form*.—Oblate.
*Axial view*.—Round.
Suture: Extends from the stem cavity, along the side, and ends about 1/2" [12.7 mm.] beyond the pistil point.
*Near the base*.—A sharp groove.
*Along the side*.—Light stitching in a shallow trough.
*Near the apex*.—A moderate groove.
Ventral surface: Rounded, very slightly lipped on both sides.
Lips: Fairly equal.
Cavity: Flaring, circular, suture showing on one side, Vivid yellow [82. v.Y] stem markings present.
*Depth*.—5/8" [15.9 mm.].
*Breadth*.—1 3/8" [34.9 mm.].
Base: Truncate.
Apex: Rounded, cordate if viewed parallel to the suture, evenly lipped.
Pistil point: Apical, negligible in length, depressed within the suture.
Stem: Medium.
*Average length*.—3/8" [9.5 mm.].
*Average width*.—3/16" [4.8 mm.].
Skin:
*Thickness*.—Medium.
*Surface*.—Pubescent.
*Density of the pubescence*.—Medium.
*Down*.—Very short, does not roll up when rubbed.
*Tenacity*.—Tenacious to flesh.
*Astringency*.—Moderate.
*Tendency to crack*.—None observed.
*Color*.—Very dark red [17. v.d.R] over a Deep reddish orange [36. deep rO] background.
Flesh:
*Color*.—Vivid yellow [82. v.Y] with moderate Strong red [12. s.R] bleeding throughout.
*Surface of pit cavity*.—Covered with Vivid yellow [82. v.Y] broken fibers when twisted away from the stone.
*Amygdalin*.—Moderate.
*Juice*.—Abundant, rich.
*Texture*.—Very firm, non-melting.
*Ripens*.—Fairly even, slightly earlier toward the apex.
*Flavor*.—Strong traditional peach flavor, moderately acidic, typically 14 brix.
*Aroma*.—Moderate.
*Eating quality*.—Very good.

STONE

Type: Clingstone.
Form: Round.
Hilum: Narrow.
Base: Rounded.
Apex: Rounded with a 1/16" [1.6 mm.] tip protruding.
Sides: Mostly equal.
Surface: Irregularly furrowed toward the apex, pitted toward the base.
Ridges: Rounded.
External color: Brilliant orange yellow [67. brill.OY].
Pit wall color when cracked: Light yellowish brown [76. l.yBr].
Cavity surface color: Moderate yellowish brown [77. m.yBr].
Average pit wall thickness: 1/4" [6.4 mm.].
Average length: 1 3/16" [30.2 mm.].
Average width: 15/16" [23.8 mm.].
Average breadth: 3/4" [19.1 mm.].
Tendency to split: None observed.
Kernel:
*Form*.—Oval.
*Skin color*.—Light yellow [86. l.Y].
*Pellicle color*.—Deep brown [56. deep Br].
*Taste*.—Sweet.
*Viable*.—Yes.
*Average length*.—11/16" [17.5 mm.].
*Average width*.—7/16" [11.1 mm.].
*Amygdalin*.—Scant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Red Princess II' peach (U.S. Plant Pat. No. 28,338) by blooming in the early season, by having large blossoms, by being self-fertile, by having reniform leaf glands, and by producing peaches that are clingstone in type, mostly red in skin color, oblate in shape, traditional peach in flavor, and non-melting in texture, but is distinguished therefrom by having a larger and more vigorous tree, by requiring less chilling hours, and by producing fruit that has more red bleeding in the flesh color, that is larger in size, that has a sweet instead of bitter kernel, and that matures about five days later.

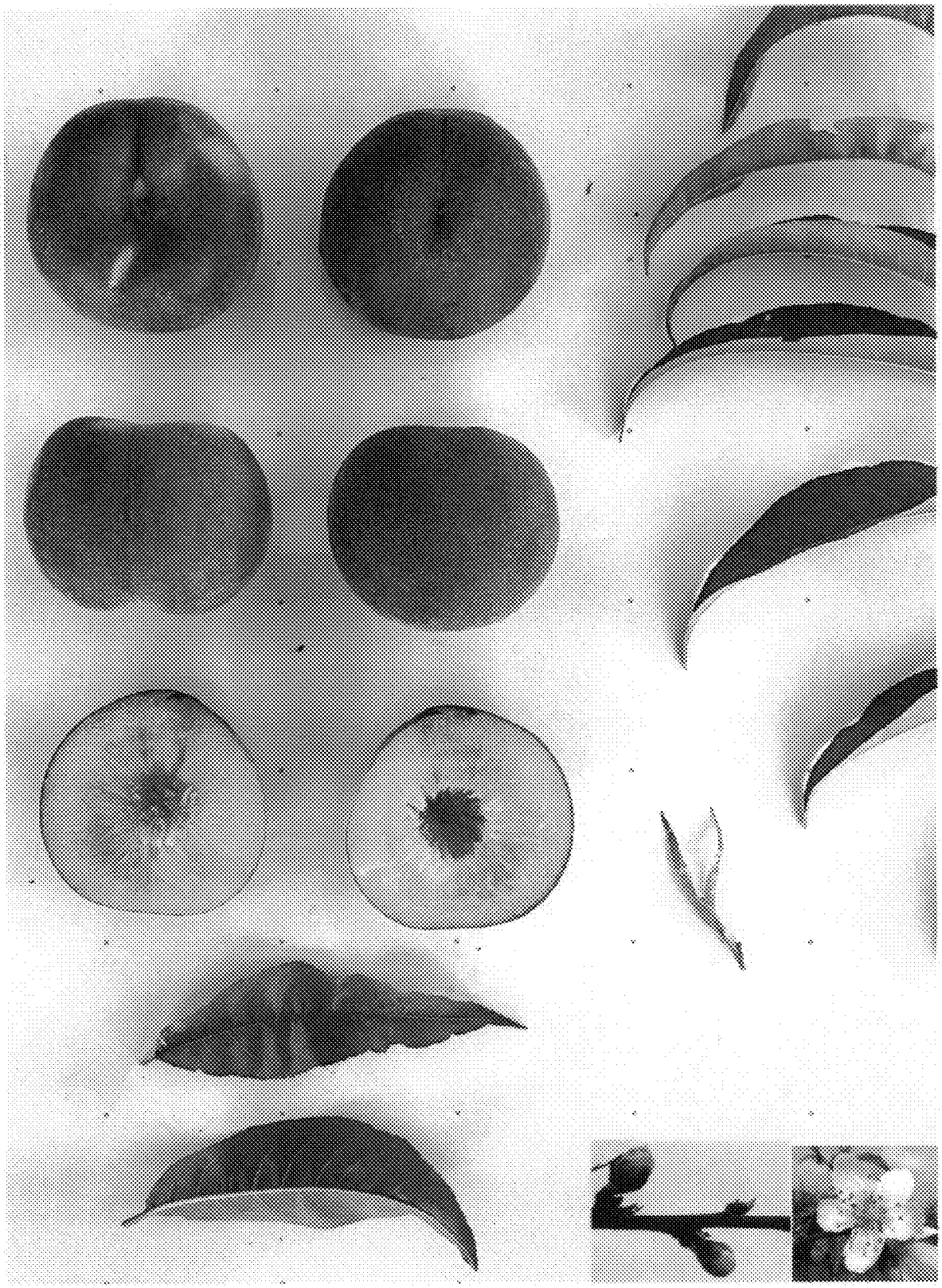

* * * * *